United States Patent [19]
Aarssen et al.

[11] Patent Number: 6,011,184
[45] Date of Patent: Jan. 4, 2000

[54] DESCALING OF BISPHENOL-A REACTOR USING WATER

[75] Inventors: Johan Adrianus Aarssen, Murcia, Spain; Gerrit Op Den Dries, Bergen Op Zoom, Netherlands; Ad Nieuwlaat, Oudenbosch, Netherlands; Marcel Vieveen, Nieuw-Vossemeer, Netherlands; Rudy Francois Alain Joseph Peemans, Erps-Kwerps, Belgium

[73] Assignee: General Electric Company, Schenectady, N.Y.

[21] Appl. No.: 09/055,590

[22] Filed: Apr. 6, 1998

[51] Int. Cl.[7] .......................... C07C 39/12; C07C 39/16; C07C 37/68
[52] U.S. Cl. .......................... 568/722; 568/723; 568/724; 568/727; 568/728
[58] Field of Search .................................. 568/727, 728, 568/724, 722, 723

[56] References Cited

U.S. PATENT DOCUMENTS

| | | | |
|---|---|---|---|
| 3,037,052 | 5/1962 | Bortnick | 560/193 |
| 3,192,270 | 6/1965 | Meyer | 568/724 |
| 4,209,646 | 6/1980 | Gac et al. | 568/724 |
| 4,346,247 | 8/1982 | Faler et al. | 568/727 |
| 4,396,728 | 8/1983 | Faler | 521/32 |
| 4,400,555 | 8/1983 | Mendiratta | 568/728 |
| 4,424,283 | 1/1984 | Faler et al. | 526/288 |
| 4,584,416 | 4/1986 | Pressman et al. | 568/727 |
| 4,766,254 | 8/1988 | Faler et al. | 568/724 |
| 4,847,433 | 7/1989 | Kissinger | 568/749 |
| 4,950,804 | 8/1990 | Iimuro et al. | 568/724 |
| 5,210,329 | 5/1993 | Gomes de Matos et al. | 568/722 |
| 5,243,093 | 9/1993 | Kissinger et al. | 568/724 |
| 5,248,839 | 9/1993 | Iimuro et al. | 568/727 |
| 5,315,042 | 5/1994 | Cipullo et al. | 568/727 |

FOREIGN PATENT DOCUMENTS

| | | |
|---|---|---|
| 0332877 | 9/1989 | European Pat. Off. . |
| 57-159733 | 10/1982 | Japan . |
| 58-135832 | 8/1983 | Japan . |

*Primary Examiner*—Gary L. Kunz

[57] ABSTRACT

An integrated process for the preparation and recovery of BPA in pure form utilizes a series of steps to crystallize the 1:1 adduct of phenol and bisphenol-A, with periodic descaling of the crystallizer surfaces with a modified reactor/crystallizer containing 1 to 40 percent water.

9 Claims, 1 Drawing Sheet

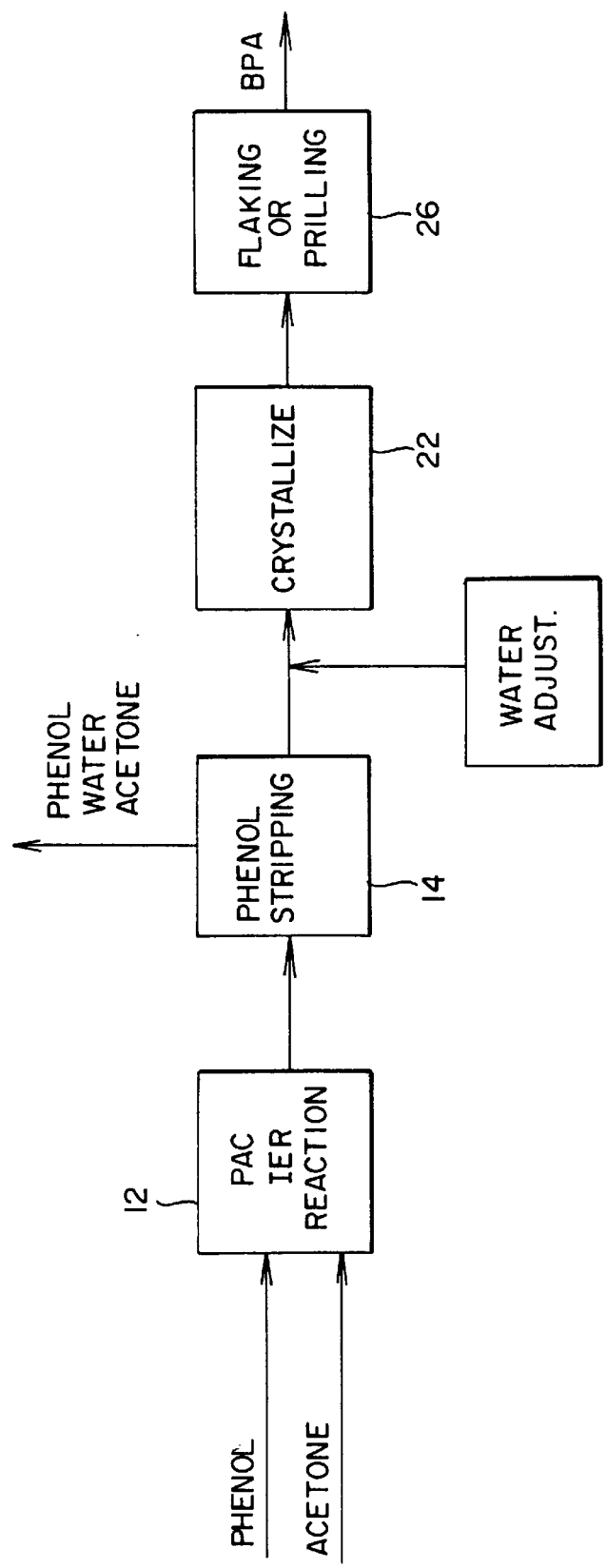

DESCALING OF BISPHENOL-A REACTOR USING WATER

BACKGROUND OF THE INVENTION

1. Field of the Invention

The invention relates to a batch, semi-continuous or continuous process for the manufacture of bisphenol-A.

2. Brief Description of Related Art

The dihydric phenol 2,2 bis(p-hydroxyphenyl) propane (commonly referred to as "bisphenol-A", "BPA" or "pp-BPA") is commercially prepared by condensing 2 moles of phenol with a mole of acetone in the presence of an acid catalyst. The phenol is present in the reaction in a molar excess of the stoichiometric requirement. During the condensation, a number of by-products such as isomeric forms of BPA are formed which are considered contaminants of the desired product, BPA. These contaminants are carried in the product stream from the condensation reaction zone, referred to as the condensation product effluent, along with water, unreacted phenol, possibly unreacted acetone and possibly trace quantities of acidic materials derived from the catalyst. Currently, the purification of the desired product BPA is a costly and multi-step procedure.

There are two commercially important processes for the synthesis of BPA currently in use. One process is sometimes called the "HCl" process, in reference to the acidic catalyst employed (hydrogen chloride).

The second synthesis involves the use of an active ion exchange catalyst and is sometimes called the "IER" process, in reference to the ion exchange resin employed. Both syntheses involve passing phenol, acetone and recycled by-products through a reactor containing an acid catalyst followed by a BPA purification scheme.

The "IER process" can be done in one of two ways; first, until essentially complete acetone depletion; second, and most desirable, is "partial acetone conversion". This technology is described in U.S. Pat. No. 5,315,042 which is hereby incorporated herein by reference thereto. The BPA reaction can be optionally promoted by the presence of a free mercaptan such as 3-mercaptopropionic acid, or use a promoter which is chemically or covalently bonded to the IER resin, or use no promoter. These resins are generally well known compositions as are methods of their preparation; see for example the preparative procedures described in U.S. Pat. No. 3,037,052 which is hereby incorporated herein by reference thereto.

The HCl process reaction effluent contains phenol, BPA, a 1:1 adduct of BPA and phenol, isomeric by-products of BPA and impurities along with the promoter (when present) and possibly unreacted acetone. This effluent, also sometimes referred to as the HCl process reaction effluent, may be fed to a stripping operation which removes the water of reaction, HCl, phenol and possibly residual acetone and/or promotor.

Representative of more detailed descriptions of the above processes for condensing phenol with acetone to obtain BPA are those found in the U.S. Pat. No. 4,346,247; 4,396,728; 4,400,555; 4,424,283; 4,584,416; 4,766,254 and 4,847,433; all of which are incorporated herein by reference thereto. The factor shared by all of these known methods and processes is the need to purify and recover the product BPA. This can be done by the 1:1 BPA/Phenol adduct crystallization (U.S. Pat. No. 5,210,329) as the desired BPA forms a 1:1 adduct with excess phenol.

The present invention is a modified process for producing purified BPA in a fully integrated, batch, semi-continuous or continuous commercial process beginning with the condensation reaction product.

SUMMARY OF THE INVENTION

The invention comprises, a process for the semi-continuous manufacture of bisphenol-A, which comprises;

(a) continuously condensing phenol with acetone in a first reaction zone in the presence of a stoichiometric excess of the phenol and a catalytic proportion of a soluble acid catalyst, whereby a condensation product effluent is obtained comprising unreacted phenol, Bis Phenol A, Bis Phenol A adducted with phenol possibly unreacted acetone and/or promotor, BPA isomers, impurities and acid catalyst;

(b) removing continuously from the first reaction zone the condensation product effluent having a given temperature preferably below the adduct crystallization temperature;

(c) batchwise completion of the reaction while precipitating crystals of BPA/phenol adduct from the reaction mixture by cooling the reaction mixture to a temperature below the BPA-Phenol adduct crystal saturation temperature by a cooled surface having a temperature lower than said temperature, whereby a portion of the precipitated crystals become affixed to said cooled surface;

(d) separating out the water, HCl and phenol, possibly unreacted phenol and/or promotor from the precipitated crystals.

Periodically and without interrupting the continuity of the aforesaid process, adjusting the water content and temperature of the first continuous reactor zone and/or the second batch reaction zone to a water content in the range of from 1 to 40 weight percent and a temperature in the range of from 40° C. to 95° C., whereby the crystals affixed to the cooled surface are dissolved.

BRIEF DESCRIPTION OF THE DRAWING

The accompanying drawing is a block diagram showing an embodiment of the process of the invention.

DETAILED DESCRIPTION OF A PREFERRED EMBODIMENT OF THE INVENTION

The commercially important processes for preparing BPA comprise condensation of 2 moles of phenol with a mole of acetone in the presence of an acid catalyst and a stoichiometric excess of the phenol reactant; see for example the U.S. Patents referred to above in the Brief Description of the Related Art. As shown in the accompanying drawing, to illustrate an embodiment process of the present invention, this reaction is the starting point of the present process which advantageously is conducted in a semi-continuous or continuous manner. In other words, the reactant phenol and acetone are fed continuously in measured proportions to the reaction zone and the product of condensation is continuously carried away from the reactor zone. Any of the previously described reaction conditions and catalysts can be employed to obtain the reaction zone effluent for continued handling according to the process of the invention.

Preferred is the condensation procedure of U.S. Pat. No. 5,315,042, incorporated herein by reference thereto, carried out semi-continuously.

As depicted in the accompanying drawing, the condensation and crystallization of BPA-Phenol adduct is carried out conventionally in a reaction zone (12). The reaction effluent containing crude BPA, phenol, isomers of BPA, impurities, water, a 1:1 adduct of phenol and bisphenol-A, other reaction by-products and possibly acetone and promoter is conventionally carried to a multiple stage recovery of acid, water and phenol followed by further purification steps.

The molten pure BPA product from the recovery unit can be recovered in a variety of forms including "flakes" by solidifying the melt on a cooled rotating drum, or as, "prills" from a prilling operation. In the reaction/crystallization unit or units, the precipitated crystals deposit on the cooler surfaces of the unit to "build-up" a deposit. When this build-up of crystals becomes problematic with regard to cooling efficiency or scales of crystals coming loose, the build-up can be removed by using the following procedure:

1 Stop the acetone feed and empty (fully or partially) the continuous or batch reactor/crystallizer.
2 Fill the reactor up with phenol, dissolve the build-up by heating the phenol/reaction mixture to 50°–90° C.
3 Start the acetone feed gently while applying HCl pressure.

These procedures interrupt the continuity of the continuous feed to the recovery/production of BPA and, accordingly, are disadvantageous.

In a continuous or semi-continuous manufacture of bisphenol, with continuous flow of product effluent from the reactor, descaling of the reaction vessels can be done with minimal/no interruption of feed of reagent to the continuous reactor by adjusting the water content & temperature of the continuous and batch reactors so as to contain 5 to 40 weight percent of water at 50–95° C. This can be accomplished by:

1. Adding water, preferably 1–40 wt % water, dosed as pure water or more preferably dosed as 1.3 to 63 wt % HCl (as a 33% solution) or a combination of water and HCl solution, to the continuous or batch reactors. During this step, it is not necessary to stop the acetone addition (if the reactor set up is continuous) or to reduce the HCl pressure.
2. Heat the reactor contents to 55°–95° C., via external heat, via heat of reaction or via heat of dissolution of the acid in the reaction medium or a combination thereof. Again, during this step, it is not necessary to stop the acetone addition (if the reactor set up is continuous) or to reduce the HCl pressure. This step is optional because, if enough water is added, the BPA phenol adduct will dissolve without extra heating.
3. If heating was applied in Step 2, cool down reactor contents gently, while continuing "normal" operation. When normal operation is resumed, the water content in the reactors will decrease to the normal level smoothly and automatically cristallisation will occur and operation will become normal.

Surprisingly, the large amount of water (of HCl) does not affect the acetone conversion or BPA finished product quality.

The results are shown in the Table, below compared to the prior art procedure of interrupting the condensation reaction to flush the reactors with hot phenol.

| | Dissolving 30% BPA crystals with Phenol (60%) and water (10%) | Dissolving BPA crystals with Phenol | Dissolving 20% BPA crystals with Phenol (72.5%), Acetone (2.5%) and Water (5%) in continuous reactor |
|---|---|---|---|
| Time needed for de-scaling operation 0–5 tons | 0.5 hours | 12 hours | 0.5 hours |
| Production loss | 0–2 tons | 35 tons | 0–5 tons |
| Minimum temperature required to dissolve 30% BPA | 70° C. | 82° C. | 60° C. |
| Quantity of phenol (or water) needed to dissolve al BPA | 5–10 tons | 25 tons phenol | 2.25 tons water |
| Acetone conversion after 6 hours | 100% | 100% | 100% |
| % o/p BPA in F.P. when cooling reactor down to 50° C. | 2500 ppm | 1850 ppm | 1850 ppm |

The concept is applicable to other commercial BPA processes employing multi-stage purification systems, such as adduct and melt crystallization (as described, for example, in U.S. Pat. No. 5,243,093).

What is claimed:

1. A process for the batch, semi-continuous, or continuous manufacture of bisphenol-A by condensing phenol with acetone, comprising forming a reaction mixture comprising acetone, an excess of the phenol and a catalytic amount of an acid catalyst in a reaction zone and at a temperature effective to produce bisphenol A and a 1:1 bisphenol-A/phenol adduct;

removing an effluent from the reaction zone, wherein the effluent comprises unreacted phenol, unreacted acetone, and the 1:1 bisphenol-A/phenol adduct;

precipitating crystals of the adduct from the reaction mixture, the effluent, or a mixture thereof, wherein at least a portion of the crystals become affixed to a surface of the reactor; and removing at least a portion of the precipitated crystals from the surface by adding water to the reaction mixture, the effluent, or a combination thereof, in an amount of 1–40% by weight of the reaction mixture, the effluent, or the combination thereof, and heating or maintaining the reaction mixture, the effluent, or a combination thereof at a temperature effective to dissolve the crystals.

2. The method of claim 1, wherein the water further comprises HCl in an amount of 1.3 to 63% by weight of the reaction mixture, the effluent, or the combination thereof.

3. The method of claim 1, wherein the water comprises HCl in an amount of 33% by weight of the water.

4. The method of claim 1, wherein the reaction mixture and added water, the effluent and added water, or the combination of reaction mixture and effluent with added water is heated to a temperature in the range from 40 to 95° C.

5. The method of claim 4, wherein the reaction mixture and added water, the effluent and added water, or the combination of reaction mixture and effluent with added water is heated to a temperature in the range from 50 to 95° C.

6. The method of claim 4, wherein the reaction mixture and added water, the effluent and added water, or the combination of reaction mixture and effluent with added water is heated to a temperature in the range from 55 to 95° C.

7. The method of claim 1, wherein the heating or maintaining is by the heat of the reaction, the heat of dissolution of the water, by application of external heat, or by a combination thereof.

8. The method of claim 1, wherein the process is a semi-continuous or continuous process employing a continuous or semi-continuous feed of acetone, phenol, or a combination thereof, and wherein removing of the crystals is done with minimal or no interruption of the continuous or semi-continuous feed.

9. The method of claim 1, further comprising cooling the heated reaction mixture, effluent, or combination thereof after the crystals have been dissolved.

* * * * *